United States Patent [19]
Diaz et al.

[11] Patent Number: 5,693,021
[45] Date of Patent: Dec. 2, 1997

[54] CATHETER EXCHANGE DEVICE

[75] Inventors: Juan Carlos Diaz, Miami; Phillip G. Reed, Davie, both of Fla.

[73] Assignee: Cordis Corporation, Miami Lakes, Fla.

[21] Appl. No.: 678,405

[22] Filed: Jul. 2, 1996

[51] Int. Cl.⁶ .................................................. A61M 5/00
[52] U.S. Cl. ...................... 604/187; 604/171; 604/194; 604/280; 604/283; 128/657; 128/772
[58] Field of Search .................................. 604/187, 264, 604/280, 283, 194, 171, 921; 128/657, 772

[56] References Cited

U.S. PATENT DOCUMENTS

| | | | |
|---|---|---|---|
| 4,846,174 | 7/1989 | Willard et al. | 606/194 |
| 5,167,641 | 12/1992 | Schmitz | 604/187 |
| 5,246,011 | 9/1993 | Caillouette | 604/187 |
| 5,290,247 | 3/1994 | Crittendon | 604/171 |
| 5,318,541 | 6/1994 | Viera et al. | 604/159 |
| 5,478,316 | 12/1995 | Bitdinger et al. | 604/187 |
| 5,484,409 | 1/1996 | Atkinson et al. | 604/191 |
| 5,545,144 | 8/1996 | Fryklund et al. | 604/187 |

*Primary Examiner*—Gary Jackson
*Attorney, Agent, or Firm*—Lockwood,Alex, Fitzgibbon & Cummings

[57] ABSTRACT

An automatic catheter exchange syringe has a biasing means which drives the syringe in a fluid expelling stroke at a single touch. The syringe includes a barrel portion with a plunger slidably disposed therein. The biasing means applies a driving force to the plunger to drive the plunger in a fluid expelling stroke at a predetermined rate. The biasing means may include compression or tension springs or a bifurcated compression spring assembly.

19 Claims, 3 Drawing Sheets

CATHETER EXCHANGE DEVICE

BACKGROUND AND SUMMARY OF THE INVENTION

The present invention relates generally to equipment employed in the performance of catheterization procedures, and more particularly, to a device used during exchange of catheter in percutaneous transluminal coronary angioplasty (PTCA) procedures.

Once arterial access is obtained, the PTCA procedure is begun by inserting a guiding catheter through the femoral, or brachial or radial artery, and advancing it until the tip of the catheter reaches the appropriate coronary ostium, or opening.

The dilatation, or balloon catheter, which is passed over a flexible steerable guidewire placed within its central lumen, is then passed through the guiding catheter until the tip, like that of the guiding catheter reaches the coronary artery opening.

With the dilatation catheter held steady, the tip of the guidewire is passed through the coronary artery until it crosses the occluding lesion and lies distal to it. The dilation catheter is then advanced over the guidewire until it also reaches the stenotic area. Once the balloon catheter is properly positioned, it is inflated multiple times as necessary to achieve an increase in arterial lumen size.

It may be necessary at times to exchange the balloon catheter either for a larger or smaller balloon size or to replace a balloon that has burst. The physician must then change balloons by drawing the balloon back along the guidewire. In order to reduce this difficulty in the exchange of balloon catheters, a physician typically injects fluid under pressure into the guidewire lumen of the balloon catheter to facilitate the movement of the balloon catheter rearwardly along the guidewire and to overcome the resistance of any bend in the guidewire. This pressurization is done with a fluid customarily used in PTCA procedures, such as a saline solution.

This pressurization is commonly performed by connecting a syringe to the guidewire lumen of the balloon catheter and injecting the fluid into the catheter by hand. Although this method is generally effective, it is difficult for a user to reliably manually apply an instantaneous injection of fluid into the catheter lumen at a pressure which is great enough to overcome the resistance of the guidewire lumen so that the balloon catheter may be easily withdrawn along the guidewire.

A catheter exchange device which reliably supplies a predetermined volume of fluid instantaneously under high pressure into the guidewire lumen of the balloon catheter during this catheter exchange with a single manual action is therefore desired.

The present invention is therefore directed to an automatic catheter exchange device which has a spring-biased syringe that supplies a predetermined volume of fluid at a preselected pressure, wherein the device is easily actuatable with a single touch.

In accordance with one aspect of the present invention, a catheter exchange device includes a syringe having a barrel portion and a piston portion slidably disposed therein, the barrel portion being partially enclosed within an exterior housing and the piston portion including a latching means by which it may be latched to the housing and maintained in a ready position for the eventual dispensing of fluids.

In another aspect of the present invention, a suitable driving means operatively connects the syringe barrel portion to the piston portion. The driving means is operable between a loaded operative position and an unloaded operative position. In the loaded position, the spring may be either compressed or placed under tension to act as a source of potential energy for driving the syringe piston portion, while in the unloaded position, the spring has released its potential energy and has driven the piston through the barrel.

In one embodiment of the present invention, the driving means includes a compression spring interconnecting the piston portion to the barrel portion such that rearward movement of the piston portion moves the spring into a loaded position where it is compressed between the piston and barrel portions. The piston portion may be latched to the barrel portion as described above to maintain the spring under compression. The latch may be operated by a user by depressing an actuating portion thereof which releases the piston portion from its latching engagement with the barrel portion whereby the piston portion is urged by the spring down the barrel portion of the syringe to thereby expel fluid stored in the barrel out of the syringe at a preselected pressure.

In yet another aspect of the present invention as incorporated in an alternate embodiment, the driving means includes a tension spring which engages the piston and barrel portions at opposite ends thereof such that by drawing the piston portion rearwardly, the spring is loaded under tension and the latch locks the piston portion into engagement with the barrel portion to retain the spring in its loaded state. Actuation of the latch in a disengagement movement releases the piston portion and the tension spring thereby draws it toward the fluid opening at the front of the syringe to expel the fluid stored in the syringe barrel under a preselected high pressure.

Accordingly, it is an object of the present invention to provide a catheter exchange device for supplying high pressure fluid into a catheter lumen during exchange or movement of a catheter during an angioplasty procedure.

It is another object of the present invention to provide a catheter exchange syringe for use in PTCA wherein the syringe includes a piston portion slidably disposed within a barrel portion, the piston and barrel portions being operatively interconnected together by a spring means such that the spring may be placed under the load during the filing of the barrel portion with a fluid. The piston is locked into this loaded position by way of a latching means, which is operable with a single finger and when actuated, releases the spring to urge the piston portion through the barrel portion.

It is yet another object of the present invention to provide an exchange syringe for use in angioplasty procedures for injecting fluid under two selected pressures through a guide catheter lumen, the exchange syringe including a variable syringe driving means including a pair of compression springs, the two springs having different spring constants, whereby one of the two springs applies a first predetermined driving force to said barrel portion and said other springs applies a second preselected during force to said barrel portion which is different than said twist force.

These and other objects, features and advantages of the present invention will be clearly understood through consideration of the following detailed description.

BRIEF DESCRIPTION OF THE DRAWINGS

In the course of the following detailed description reference will be frequently made to the accompanying drawings in which.

3

Figure 1:
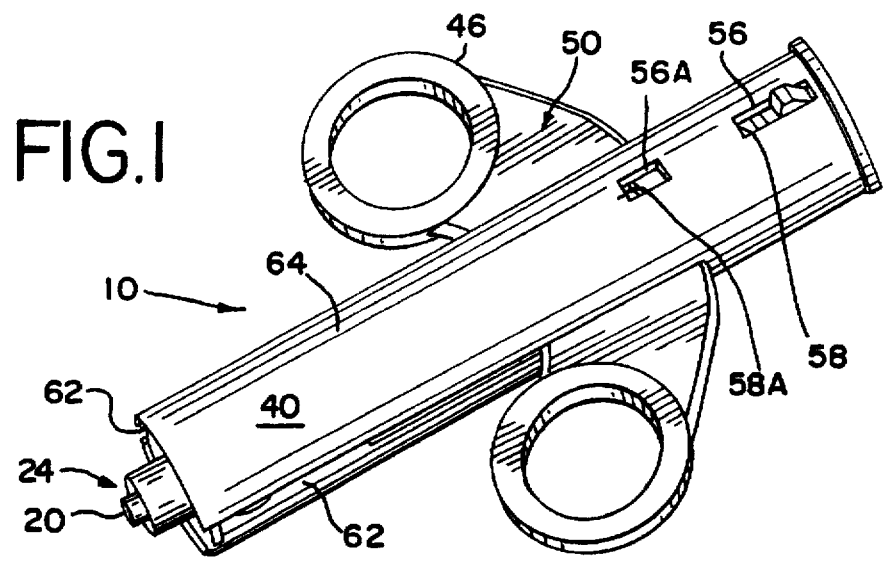
FIG. 1 is a perspective view of a first embodiment of a catheter exchange device constructed in accordance with the principles of the present invention.
Figure 2:
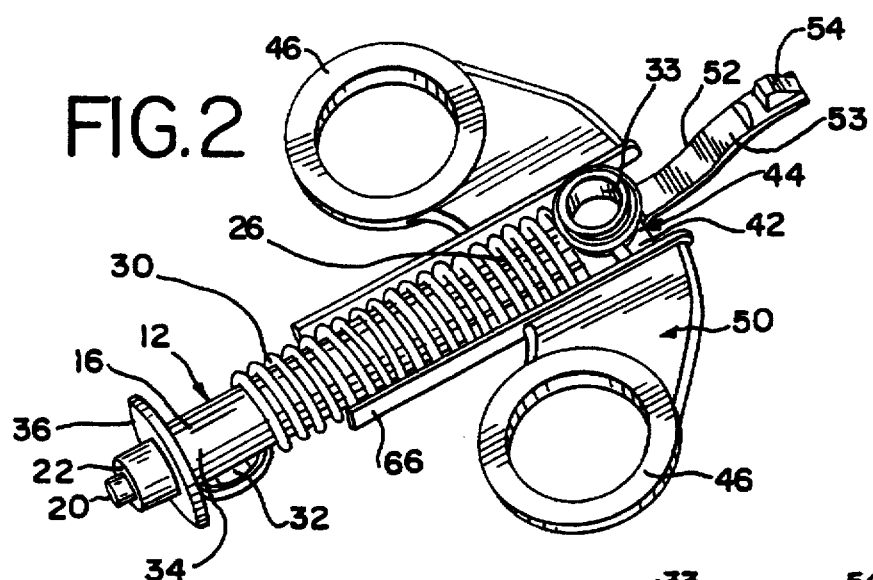
Figure 3:
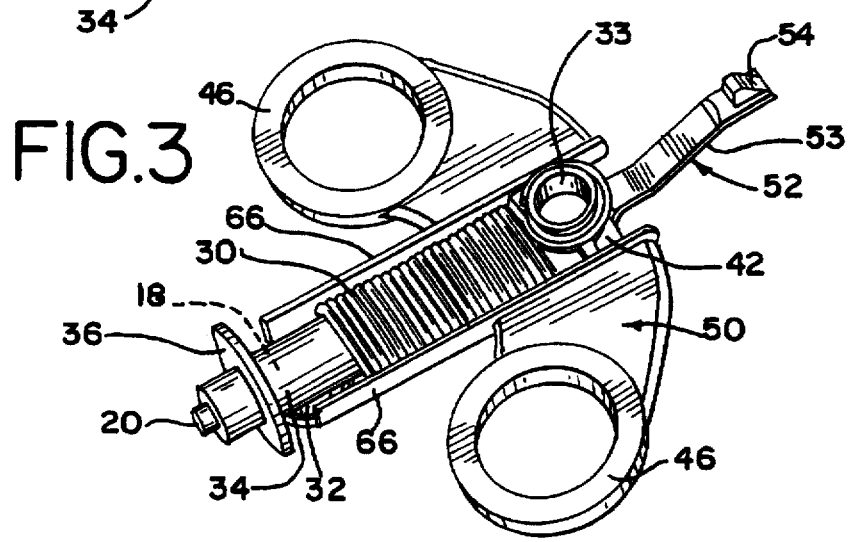
Figure 4:
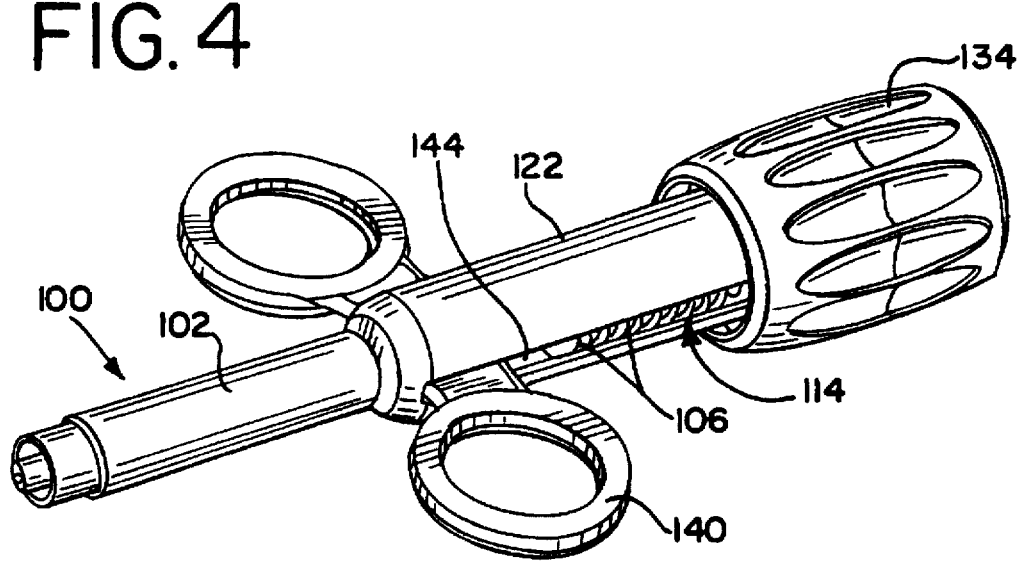
Figure 5:
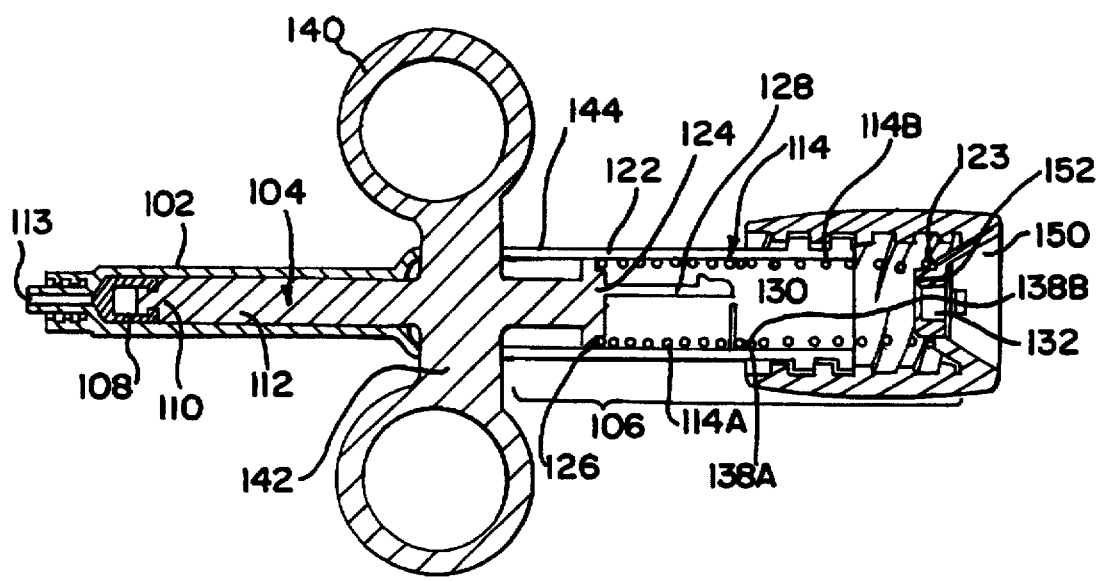
Figure 6:
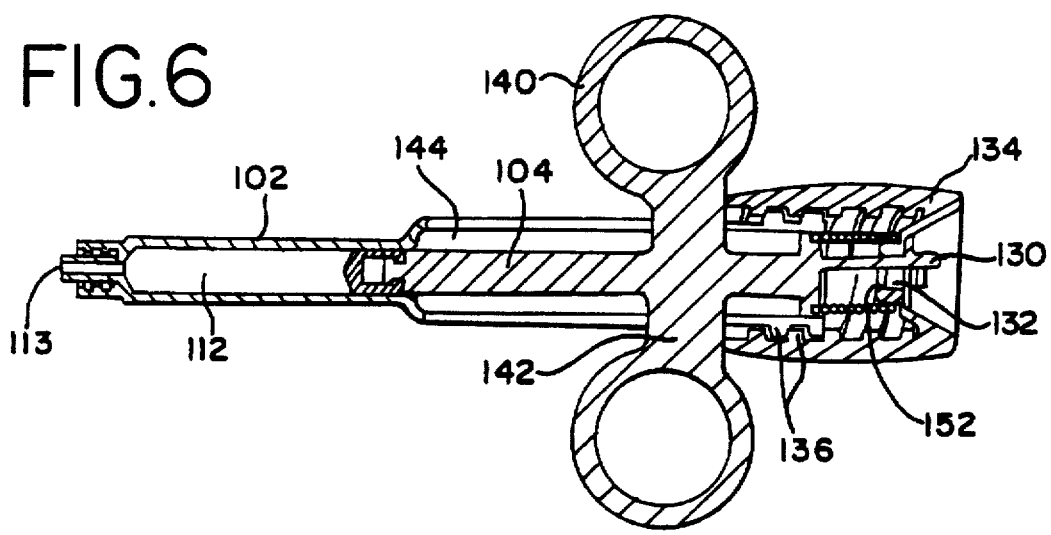
Figure 7:
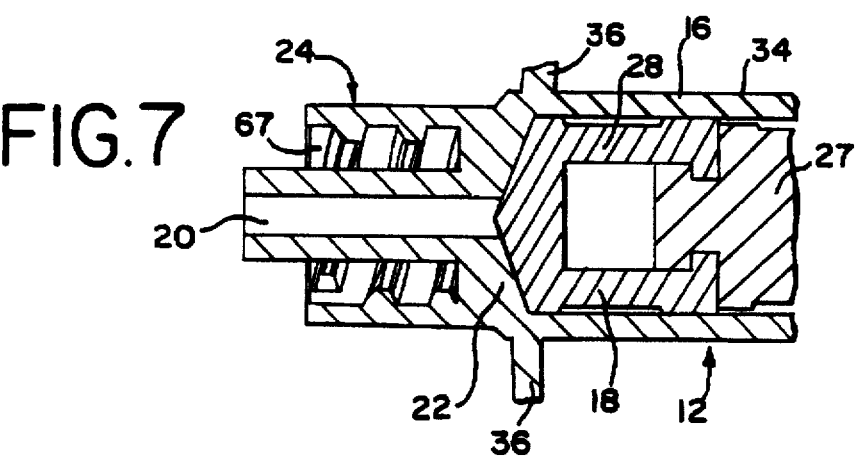
Figure 8:
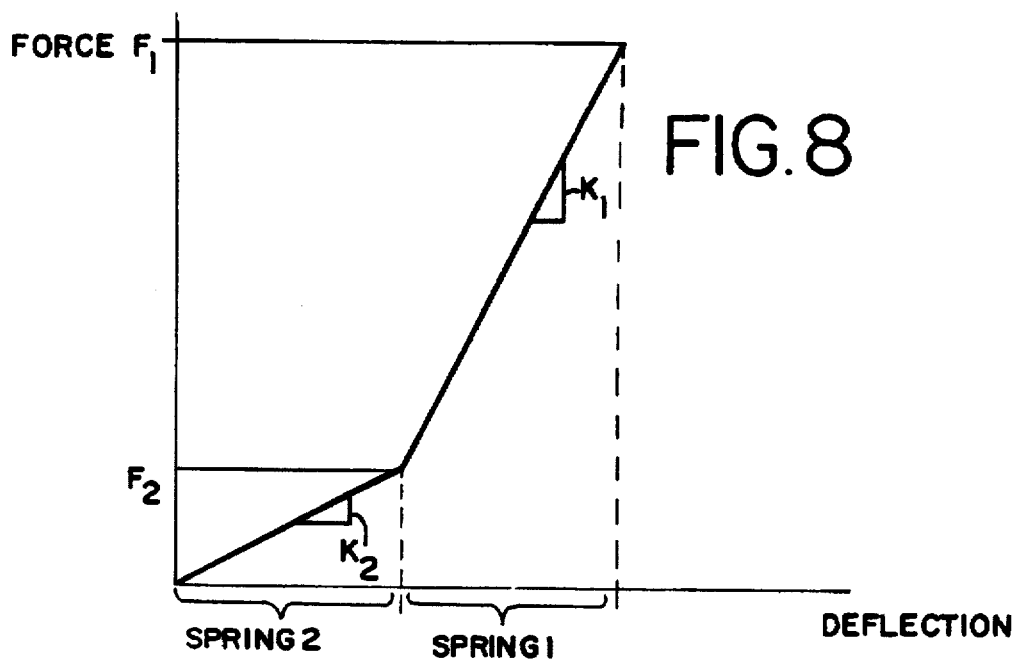

FIG. 2 is a perspective view of the catheter exchange device in a loaded, or tensioned state, of FIG. 1 with its exterior housing removed;

FIG. 3 is the same view as FIG. 2 but in an unloaded, or untensioned state;

FIG. 4 is a perspective view of a second embodiment of a catheter exchange device constructed in accordance with the principles of the present invention;

FIG. 5 is a sectional view of the catheter exchange device in an unloaded state taken along lines 5—5 of FIG. 4;

FIG. 6 is the same view as FIG. 5, but illustrating the catheter exchange device in a loaded state;

FIG. 7 is an enlarged sectional view of the formed tip end of the piston of the catheter exchange device of FIG. 4; and FIG. 8 is a schematic diagram of the operation of the catheter exchange device.

DETAILED DESCRIPTION OF THE PREFERRED EMBODIMENTS

A catheter exchange device constructed in accordance with the principles of the present invention is shown generally at 10, and includes a syringe 12 having an elongated cylindrical barrel 16 with an internal fluid bore 18 which serves as a reservoir for fluids. The syringe barrel 16 has a fluid outlet 20 located in a forward endwall 22 thereof disposed at the front end 24 of the device 10. The syringe barrel 16 and its associated piston 26 are enclosed within an exterior housing 40.

The syringe piston 26 is slidably disposed within the barrel 16 and has an elongated shaft portion 27 and a front tip or seal portion 28. As is known in syringe construction, the shaft and seal portions 27, 28 of the piston 26 are telescopically received within the barrel 16 such that the seal portion 28 provides a fluid tight seal between the barrel sidewall and the piston shaft 27. The barrel 16 defines a pumping chamber of variable volume which extends between the barrel outlet 20 and the tip 28 of the piston 26.

As mentioned above, one of the benefits of the present invention resides in the ability of the user to discharge fluid from the bore 18 of the syringe portion 12 in a single step. In order to accomplish this, the exchange device 10 of the present invention includes a means for driving the piston 26 in a fluid discharge stroke within the barrel 16. Such a driving means is illustrated in the first embodiment 10 of FIG. 1–3 as a coil spring 30 extending between the syringe barrel 16 and piston 26 and further engaging two opposing members, illustrated in FIG. 2 as posts 32, 33 which extend outwardly from the syringe barrel and piston 16, 26 respectively.

The spring 30 includes two end hooks 31 at its opposite ends for engagement with the posts 32, 33. The first of these two engagement posts 32 is disposed on the exterior surface 34 of the barrel 16 proximate to and behind a circular skirt wall 36 which extends outwardly from the barrel 16 into engagement with an annular groove 38 formed on the inside surface of the device housing 40. The other of the two engagement posts 33 is formed on the piston 26, preferably on a transverse portion thereof 42, which defines a surface 44 extending sideways between two finger rings 46 of a syringe driving and loading assembly 50. The assembly 50 provides a means for the user to apply a bias to the spring 30 and place the spring 30 into a loaded position as well as drive the syringe piston 26 at a single touch.

The spring 30 of the driving means is operable between two positions. In one of these operative positions, illustrated

4 in FIG. 2, the spring 30 is in a loaded position, that is, it is biased by an external load applied to it other than a preload, if desired. This bias is applied by a user drawing the driving and loading assembly 50 rearwardly with one hand. In this regard, the spring is extended past its free length (compressed as shown in FIG. 6). In this position, the piston 26 is extended rearwardly in the syringe barrel 16 which is the normal piston position when the bore 18 is filled with a desired fluid for injection. The circular skirt of the barrel is fixed in place within the device 10 relative to the piston 16 so that when the piston 26 is drawn rearwardly within the housing 40 (and barrel 16) as shown in FIG. 2, the spring 30 is placed under tension.

The driving and loading assembly 50 preferably includes a means for retaining the spring 30 in its loaded position, where it serves as a source of potential energy for driving the piston 26, illustrated in the Figures as a latching member 52 which extends rearwardly from the piston 26 and which includes a latching lug 54 thereon extending radially outwardly from the latching member 52 as illustrated. The latching member 52 and its associated lug 54 are preferably aligned with a latching opening 56 formed in a sidewall 57 of the device housing 40 and the latching member 52 preferably has an angled portion 53 which extends toward the housing 40. The opening 56 of the housing 40 includes an engagement surface 58 which opposes the latching lug 54 such that the lug 54 and surface 58 engage each other to retain the spring 30 in its loaded position.

The housing 40 may be provided with additional latching openings, such as 56A which include associated confronting engagement surfaces 58A in order to apply different degrees of tensions to the spring 30 as well as to control the distance which the piston 26 travels within the syringe barrel. In order to facilitate entry of the latching lug 54 into the housing engagement openings 58, the lug may be provided with a slanted rear surface 55 as illustrated which acts as a ramp or cam surface when the assembly 50 is drawn rearwardly in the housing 40.

In order to facilitate the loading of the spring and latching of the syringe into a loaded position as mentioned above, the device 10 preferably includes a manipulatable portion, illustrated as two finger rings 46 extending out from the piston shaft 27 along the sides of the device 10 and through two longitudinal slots 62 disposed within a sidewall 64 of the housing 40. Theses rings 46 accommodate the fingers of a user and define a portion of the syringe 12 which the user may grasp in order to draw the piston 26 rearwardly in the barrel 16, thereby loading the spring 30 and drawing fluid into the bore 18 of the syringe portion 12. Movement of these rings 46 by the user also results in drawing the latching lug 54 into engagement with the housing opening 56.

To facilitate the motion which occurs when the latching lug 54 is released, the piston shaft 27 may include a pair of elongated runners 66 which extend longitudinally and spaced apart from the piston shaft 27. These runners 66 may engage corresponding grooves (not shown) in the device housing 40.

As is known in the art, the syringe 12 includes a means for engaging a port of a catheter, shown as a luer lock 67 disposed at the forward tip of the syringe 12, in order to provide a reliable connection with the catheter.

Turning now to FIGS. 4–6, a second embodiment of a catheter exchange device constructed in accordance with the principles of the present invention is illustrated generally at 100. The structure of this embodiment 100 is similar to that of the first embodiment in that it includes an elongated syringe barrel portion 102, an elongated plunger 104 slidably disposed therein and a plunger driving assembly 106 operatively interconnected to the plunger 104. The plunger 104 has a syringe tip 108 at its forward end 110. The plunger slides within the bore 112 of the syringe barrel 102 under urging of the driving assembly 106 to expel fluids from the bore 112 through a fluid outlet 113. The forward end 110 of the barrel portion 102 has an internal section which enables its connection to a catheter port, such as the luer threads 111 illustrated.

The device further includes a housing 120 which is elongated and which has two distinct sections: a forward barrel portion 102 and a rearward housing portion 122. The housing portion 122 houses the plunger driving assembly 106 and has a diameter which is greater than the forward barrel portion 102. The housing portion 122 accommodates the plunger 104 throughout its movement within the device 100. Preferably, the barrel portion 102 will be clear or transparent so the attending physician may view the discharge.

The driving assembly 106 is disposed in the housing portion 122 of the device 100 between the plunger 104 and a spring engagement surface 123 and includes a pair of manually grippable members, such as finger rings 140 extending transversely from a cross member 142 through housing slots 144. The plunger 104 includes a stop surface 124 on a rear portion thereof in the form of an annular rim 126 which provides a seat for one end of the driving assembly 106 and defines a moveable surface against which the spring 114 acts in both compression and expansion.

Interior of the stop surface 124, a latching member 128 extends longitudinally from the plunger 104 and terminates in a latching lug 130. This lug 130 is aligned with an opening 132 formed in a spring adjustment endcap 134 which engages the outer surface of the housing portion 122 by way of suitable threads 136. The threaded engagement between the endcap 134 and the housing portion 122 permits the endcap 134 to be moved axially along the housing portion outer surface in a manner well known in the art. This movement permits a user to selectively adjust the extent of compression of the driving assembly spring 114.

In an important aspect of the second embodiment 100, the driving assembly 106 may have as its spring, a pair of compression springs 114A, 114B which preferably each have different spring constants to provide two different levels, or rates, of plunger displacement. In this regard, the rearmost spring 114B may have a greater spring constant than the forward spring 114A so that, in practice the rearmost spring 114B may have a spring force or constant which will displace the plunger at 10 atmospheres of pressure, while the forward spring 114A may have a lesser spring force or constant, equivalent to about 2 atmospheres. Thus it can be seen that the pressure of fluid injection with the device 100 may be controlled in order to provide an initial fluid injection at high pressure and then taper down to a lower, declining pressure.

This pressure bifurcation will permit the physician to easily initially move the catheter rearwardly along the guidewire to properly seat the catheter as the guidewire leaving its distal end free, at which point the catheter may be completely withdrawn from the patient along the guidewire without fear of losing control of the withdrawal rate of the catheter.

FIG. 8 is a graph illustrating the bifurcated spring action which occurs in the second embodiment 100. The first spring 114B, (spring$_1$ in FIG. 8) has a given spring constant $K_1$ while the second spring 114B (spring$_2$ in FIG. 8) has a different but lower spring constant $K_2$. When the latching lug 130 is released, the syringe plunger 104 is driven formally at a linear rate equal to $K_1$, the slope of the rightmost curve of FIG. 8. When that spring 114B (spring$_1$) has fully expanded, the expansion of the second spring 114A (spring$_2$) begins at a different linear rate than the first one equal to $K_2$, the slope of the leftmost curve of FIG. 8.

Returning to FIG. 5, the two springs 114A, 114B are of the same overall diameter, corresponding generally to the interior diameter of the housing 122. The springs 114A, 114B are arranged in the housing 122 longitudinally so that their opposing ends 138A, 138B engage each other in an abutting engagement. The spring constant and resultant force which the springs 114A, 114B will exert on the plunger 104 may be largely controlled by the diameter of the spring wire. As shown, the rear spring 114B has a larger diameter wire than the forward spring 114A. This bifurcated force application may be accomplished in other ways evident to one skilled in the art.

The adjustment endcap latch opening 132 is preferably centrally disposed in the endcap 134 so that the latching lug 130 may protrude therethrough into a central recess 150 such that a user may easily move the lug 130 with one finger to release the lug 130 from its engagement with the endcap 132. The opening 132 may include angled, or ramped interior surfaces 152 to facilitate the entry of the latching lug 130 into and through the opening 132.

The catheter exchange device of the present invention is simple and convenient to use. It may be fabricated inexpensively and the syringe elements may, if desired, be made of inexpensive disposable materials such as plastics, thereby eliminating the need for sterilization and/or disinfection after every use. The present invention therefore provides an automatic syringe capable of injecting fluid into a catheter at a predetermined rate, without the need for manual injection of fluid.

While the preferred embodiments of the invention have been shown and described, it will be apparent to those skilled in the art that changes and modifications may be made therein without departing from the spirit of the invention, the scope of which is defined by the appended claims.

We claim:

1. An automatic syringe device for injecting fluids into a catheter at a predetermined rate to create a desired pressure head within said catheter which facilitates exchange of catheters during angioplasty procedures, comprising:

a barrel portion having an internal bore of a preselected diameter and volume, a plunger portion slidably disposed within the barrel portion, said barrel portion having a front end with an outlet disposed therein which defines a fluid passage communicating with said internal bore and leading out of said barrel portion, said barrel portion further having means associated with said front end thereof for effecting a connection between said barrel portion and the catheter, means for driving said plunger portion forwardly within said barrel portion to expel fluids from said barrel portion into said catheter at the predetermined rate, said plunger portion driving means being operable between two operative positions, one of said two positions being an unloaded position wherein said driving means moves said plunger portion forwardly in said barrel portion and the other of said two positions being a loaded position wherein said driving means retains said plunger portion rearwardly in said barrel portion.

2. The catheter exchange device as defined in claim 1, wherein said plunger portion driving means includes spring means disposed between said barrel portion and said plunger portion.

3. The catheter exchange device as defined in claim 2, wherein said spring means includes a compression spring.

4. The catheter exchange device as defined in claim 2, wherein said spring means includes a tension spring.

5. The catheter exchange device as defined in claim 1, wherein said plunger portion driving means further includes means for manually drawing said plunger portion into said loaded position, including two elongated members extending outwardly from said plunger portion and presenting two manually engageable surfaces on opposite sides of said syringe.

6. The catheter exchange device as defined in claim 5, wherein said catheter engagement means includes a luer lock portion.

7. The catheter exchange device as defined in claim 5, wherein said plunger portion drawing means includes a pair of ring members defining two surfaces engageable by a user's fingers.

8. The catheter exchange device as defined in claim 1, further including a housing partially enclosing at least a portion of said plunger portion, said plunger portion being slidably disposed within said housing.

9. The catheter exchange device as defined in claim 8, wherein said plunger portion driving means includes a compression spring disposed within said housing and extending between a rear surface of said plunger portion and an end surface of said housing, whereby rearward movement of said plunger portion compresses said compression spring between said two surfaces into said loaded position, said device further including means for latching said plunger in said loaded position and means for actuating said latching means in order to release said plunger portion from said loaded position.

10. The catheter exchange device as defined in claim 8, wherein said plunger portion driving means includes a first engagement post disposed on said barrel portion, a second engagement post disposed on said plunger portion and spaced apart from said first engagement post and a tension spring extending therebetween in engagement said first and second engagement posts, whereby rearward movement of said plunger portion applies tension to said tension spring.

11. The catheter exchange device as defined in claim 1, further including means for latching said plunger portion into said loaded position.

12. The catheter exchange device as defined in claim 11, wherein said latching means includes an elongated latching member extending axially from said plunger portion, said latching member further being aligned and engageable with a confronting fixed surface of said device.

13. The catheter exchange device as defined in claim 1, further including a housing enclosing said barrel portion and said plunger portion driving means, said plunger portion driving means including a pair of compression springs disposed between said plunger portion and said housing, each of said springs being capable of exerting a different spring force on said plunger portion to thereby expel fluids from said barrel portion at two predetermined rates.

14. The catheter exchange device as defined in claim 13, further including an endcap threadly engaging said housing, said endcap having an internal face defining said housing end surface which engages an end of one of said compression springs, said endcap being manually advanceable on said housing, whereby advancement of said endcap increases the compression of said springs so as to selectively adjust the spring force of said springs and thereby selectively control the rate at which fluids are expelled from said barrel portion by said plunger portion.

15. The catheter exchange device as defined in claim 1, further including a housing enclosing said barrel portion and said plunger portion, said device further including a latching member extending from said plunger portion for retaining said plunger portion in said loaded positions, the latching member including a latching surface which engages an opposing surface disposed on said housing, said latching member partially extending through said housing when engaged with said housing opposing surface.

16. The catheter exchange device as defined in claim 15, further including an adjustment member threadedly engaging said barrel portion, the adjustment member including an opening aligned with said latching member and which receives said latching member, said adjustment member further including a recess surrounding said opening.

17. A catheter exchange syringe for automatically injecting at the touch of an actuator fluids into a catheter lumen, comprising: an elongated hollow barrel and a piston slidably disposed therein, said barrel being defined by a sidewall and a frontwall, the frontwall having an opening disposed therein which communicates with said barrel and defines a fluid outlet of said syringe by which fluids may be drawn into and expelled from said syringe barrel, the piston having an elongated shaft and tip portion, said piston further including a pair of manipulation members extending crosswise from said shaft, said manipulation members providing two surfaces engageable by the hand of a user which permits the user to draw said piston rearwardly within said barrel to fill said barrel with a fluid, said syringe further including biasing means for applying an ejection force to said piston to drive said piston forwardly within said barrel in order to expel fluid from said barrel through said syringe fluid outlet, said biasing means operatively interconnecting said piston to said barrel and being further operable between first and second operative positions, the first position being wherein said biasing means stores potential energy and said piston is disposed rearwardly within said barrel, the second position being wherein said biasing means has released its stored potential energy and said piston is disposed forwardly within said barrel, said syringe still further including a housing extending from said barrel sidewall, the housing partially enclosing said piston shaft, said piston including a latching member extending from said piston shaft and moveable with said piston, said latching member engaging a confronting engagement face of said housing in order to retain said piston in said first position, said latching member being easily actuatable and disengageable from engagement with said confronting engagement face by a simple manual movement to thereby release said potential energy stored in said biasing means and thereby drive said piston forwardly within said barrel and expel fluid contained in said barrel from said syringe at a preselected rate.

18. The catheter exchange syringe as defined in claim 17, wherein said biasing means includes a pair of compression springs axially aligned and disposed in said housing, said springs having different spring constants to exert a combined bifurcated spring force upon said piston when said latch member is disengaged to thereby expel fluids contained in said syringe at two different preselected rates.

19. The catheter exchange syringe as defined in claim 18, wherein said housing includes an adjustment member moveable on said housing, said springs being disposed between said piston and a confronting face of said adjustment member, said adjustment member being moveable on said housing to selectively vary the compression of said springs to thereby selectively vary the fluid expelling rate.

* * * * *